United States Patent
Efrahimi

(10) Patent No.: US 9,017,738 B2
(45) Date of Patent: Apr. 28, 2015

(54) COMPOSITION FOR TREATING HEMORRHOIDS

(71) Applicant: Eyal Efrahimi, Jerusalem (IL)

(72) Inventor: Eyal Efrahimi, Jerusalem (IL)

(*) Notice: Subject to any disclaimer, the term of this patent is extended or adjusted under 35 U.S.C. 154(b) by 0 days.

(21) Appl. No.: 13/769,848

(22) Filed: Feb. 19, 2013

(65) Prior Publication Data

US 2014/0234453 A1  Aug. 21, 2014

(51) Int. Cl.
*A61K 36/63* (2006.01)
*A61K 36/61* (2006.01)
*A61K 36/54* (2006.01)
*A61K 36/24* (2006.01)

(52) U.S. Cl.
CPC .............. *A61K 36/63* (2013.01); *A61K 36/54* (2013.01); *A61K 36/61* (2013.01); *A61K 36/24* (2013.01)

(58) Field of Classification Search
CPC ....... A61K 36/61; A61K 36/63; A61K 36/54; A61K 36/24; A61K 2300/00
USPC ....................................................... 424/725
See application file for complete search history.

(56) References Cited

U.S. PATENT DOCUMENTS

2011/0274772 A1 * 11/2011 Kucukay et al. .............. 424/727

FOREIGN PATENT DOCUMENTS

IT    2002-MI2263 A1 * 4/2004

* cited by examiner

*Primary Examiner* — Susan Hoffman
(74) *Attorney, Agent, or Firm* — Mark M. Friedman

(57) ABSTRACT

The composition for treating hemorrhoids includes dry components: oleander (*nerium oleander*), myrtle (*myrtus communis*) and bay laurel (*laurus nobilis*), which are then mixed into a homogenous solution with olive oil. In the preferred embodiment, the composition for treating hemorrhoids includes the following components: 30%-70% by weight of olive oil, 27%-44% by weight of oleander (*nerium oleander*), 15%-25% percentage by weight of myrtle (*myrtus communis*) and 5%-15% percentage by weight of bay laurel (*laurus nobilis*). For the most preferred embodiment, for 1 liter (about 1000 cubic centimeters) of olive oil, 1000 cubic centimeters (cc) of the dry components of the composition may include 70% percentage by weight of oleander (*nerium oleander*), 20% percentage by weight of myrtle (*myrtus communis*), and 10% percentage by weight of bay laurel (*laurus nobilis*).

3 Claims, No Drawings

COMPOSITION FOR TREATING HEMORRHOIDS

FIELD OF THE INVENTION

This invention relates to the medical field and, more particularly, to a composition for treating hemorrhoids.

BACKGROUND OF THE INVENTION

Hemorrhoids are vascular structures in the anal canal which help with stool control. They become pathological or piles when swollen or inflamed. In their physiological state, they act as a cushion composed of arterio-venous channels and connective tissue.

The symptoms of pathological hemorrhoids depend on the type present. Internal hemorrhoids are usually associated with painless rectal bleeding. External hemorrhoids may produce few symptoms; but, if thrombosed, there can be significant pain and swelling in the area of the anus. While the exact cause of hemorrhoids remains unknown, a number of factors which increase intra-abdominal pressure, in particular constipation, are believed to play a role in their development.

Initial treatment for mild to moderate hemorrhoid discomfort or disease consists of increasing fiber intake, oral fluids to maintain hydration, nonsteroidal anti-inflammatory drugs to help with the pain, and rest. A number of minor procedures may be performed if symptoms are severe or do not improve with conservative management. Surgery is reserved for those who fail to improve following these measures.

While many topical agents and suppositories are available for the treatment of hemorrhoids, there is little evidence to support their use. Steroid containing agents should not be used for more than 14 days, as they may cause thinning of the skin. Most agents include a combination of active ingredients. These may include: a barrier cream such as petroleum jelly or zinc oxide, an analgesic agent such as lidocaine, and a vasoconstrictor such as epinephrine. Flavonoids are of questionable benefit with potential side effects.

Kucukay (EP 2022504 and Wo 2010/081485) discloses a composition for the treatment of haemorrhoids comprising aqueous extracts of fig leaves, walnut shells and/or artichoke leaves, in particular in combination with aqueous extracts of horse chestnuts.

Rolf (WO 2008/133982) discloses Adhesive patches that are applied to the skin for the transdermal or topical delivery of a medication.

McAnalley (WO 2009/0177088) discloses hydrogel wound dressings that are made entirely of naturally occurring food ingredients, and optionally with safe food additives.

Schultz (WO 2001/028491) discloses a topical composition for the treatment of a dermatologic disease that includes a carrier, at least one essential oil and a dermatologic active ingredient having a therapeutic effect for the dermatologic disease.

Therefore, there is a need for an effective, safe and simple composition for treating hemorrhoids.

SUMMARY OF THE INVENTION

These and other objects of the invention are achieved with a composition for treating hemorrhoids that includes dry components: oleander (*nerium oleander*), myrtle (*myrtus communis*) and bay laurel (*laurus nobilis*), which are then mixed into a homogenous solution with olive oil.

According to the Invention, in the preferred embodiment, the composition for treating hemorrhoids includes the following components: 30%-70% by weight of olive oil, 27%-44% by weight of oleander (*nerium oleander*), 15%-25% percentage by weight of myrtle (*myrtus communis*) and 5%-15% percentage by weight of bay laurel (*laurus nobilis*).

In a preferred embodiment, for 1 liter (about 1000 cubic centimeters) of olive oil, 1000 cubic centimeters (cc) of the dry components of the composition may include 70% percentage by weight of oleander (*nerium oleander*), 20% percentage by weight of myrtle (*myrtus communis*), and 10% percentage by weight of bay laurel (*laurus nobilis*).

Other objects, features and advantages of the present invention will become apparent upon reading the following detailed description in conjunction with the drawings and the claims.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

According to the Invention, the composition for treating hemorrhoids includes the following three dry components: oleander (*nerium oleander*), myrtle (*myrtus communis*) bay laurel (*laurus nobilis*). These dry ingredients are then mixed with olive oil to form a homogeous hemorrhoid treatment compound.

For purposes of conversion herein, 1 cubic centimeter equals 0.001 liters.

In the preferred embodiment of the Invention, the composition for treating hemorrhoids includes the following components: 30%-70% by weight of olive oil, 27%-44% by weight of oleander (*nerium oleander*), 15%-25% percentage by weight of myrtle (*myrtus communis*) and 5%-15% percentage by weight of bay laurel (*laurus nobilis*).

In a preferred embodiment, for 1 liter (about 1000 cubic centimeters) of olive oil, 1000 cubic centimeters (cc) of the dry components of the composition may include 70% percentage by weight of oleander (*nerium oleander*), 20% percentage by weight of myrtle (*myrtus communis*), and 10% percentage by weight of bay laurel (*laurus nobilis*).

*Nerium oleander* has been reported in ancient texts and folklore for more than 1500 years. It has been used traditionally by herbalists as a folk remedy for a wide variety of maladies and conditions, including dermatitis, abscesses, eczema, psoriasis, sores, warts, corns, ringworm, scabies, herpes, skin cancer, asthma, dysmenorrheal, epilepsy, malaria, abortifacients, emetics, heart tonics, and tumors. Macerated leaves of oleander have been applied topically for treatment of dermatitis, loss of hair, superficial tumors and syphilis. A decoction of oleander leaves has been used for the treatment of gingivitis and as a nose drop for children. The application of nerium oleander cardiac glycosides applied intramuscularly (IM) and orally to combat cancers is now being investigated. The National Cancer Institute has defined oleandrin, one of the principal glycosides in *Nerium oleander*, as "A lipid soluble cardiac glycoside with potential antineoplastic activity." It has not heretofore been know, however, for treating hemorrhoids.

Evidence from epidemiological studies suggests that a higher proportion of monounsaturated fats in the diet is linked with a reduction in the risk of coronary heart disease. This is significant because olive oil is considerably rich in monounsaturated fats, most notably oleic acid. Consumption of olive oil can provide heart health benefits such as favorable effects on cholesterol regulation and LDL cholesterol oxidation, and that it exerts antiinflamatory, antithrombotic, antihypertensive as well as vasodilatory effects both in animals and in humans. Additionally, olive oil protects against heart disease as it controls the "bad" levels of LDL cholesterol and raises levels of the "good" cholesterol, HDL. It has not heretofore been know, however, for treating hemorrhoids.

In the preferred embodiment, extra virgin or first pressed olive oil is used.

In several countries, particularly in Europe and China, there has been a tradition for prescribing myrtle for sinus infections; but, a systematic review of herbal medicines used for the treatment of rhinosinusitis concluded that the evidence that any herbal medicines are beneficial in the treatment of rhinosinusitis is limited. It has not heretofore been know, however, for treating hemorrhoids.

Aqueous extracts of bay laurel can also be used as astringents and even as a reasonable salve for open wounds. In massage therapy, the essential oil of bay laurel is reputed to alleviate arthritis and rheumatism. In aromatherapy, it is used to treat earaches and high blood pressure. The chemical compound lauroside B isolated from *laurus nobilis* is an inhibitor of human melanoma (skin cancer) cell proliferation at high concentrations. It has not heretofore been know, however, for treating hemorrhoids.

To make the hemorrhoid compound, there is processing of oleander (nerium oleander), myrtle (*myrtus communis*) and bay laurel (*laurus nobilis*) to a fine dry composition wherein their active ingredients are released. More specifically, first the dry components—oleander (*nerium oleander*), myrtle (*myrtus communis*) and bay laurel (*laurus nobilis*)—are finely chopped, milled and/or crushed. This may preferably be done by any conventional electric blender. For small quantities it may even be done with a mortar and pestle.

Then, a corresponding amount of olive oil is boiled. In most cases the volume amount of olive oil will approximately correspond to the cubic volume of the processed dry ingredients. Preferably, 1 liter of olive oil is used.

After the olive oil starts to boil, the processed dry components are added to the olive oil, and the mixture is boiled for one (1) minutes. Preferably the mixture is stirred during the boiling.

Thereafter, the mixture is allowed to cool to room temperature (about 20° C.).

The mixture is then re-boiled for another minute. After this second boiling it cools to room temperature (about 20° C.). In some cases a third boiling may be useful, followed by cooling to room temperature The cooling and boiling of the compound causes the dry plant ingredients to release their active ingredient effectively. By first finely chopping, milling and and/or crushing and then boiling the dry plant ingredients, it causes the release of their active ingredients into the olive oil. This results in a mixture of olive oil+active ingredients that are found in the leaves.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

The invention claimed is:

1. A composition for treating hemorrhoids comprising: 30%-70% by weight of olive oil, 27%-44% by weight of oleander, 15%-25% percentage by weight of myrtle and 5%-15% percentage by weight of bay laurel, and having no other active ingredients.

2. The composition of claim 1 wherein olive oil being 50% percentage by weight of the composition, oleander being 35% percentage by weight of the composition, myrtle being 10% percentage by weight of the composition, and bay laurel being 5% percentage by weight of the composition.

3. The composition of claim 1 wherein the composition contains 1 liter of olive oil and 1000 cubic centimeters (cc) of dry components including 70% percentage by weight of oleander, 20% percentage by weight of myrtle, and 10% percentage by weight of bay laurel.

* * * * *